United States Patent [19]
Keller et al.

[11] Patent Number: 5,897,510
[45] Date of Patent: Apr. 27, 1999

[54] METHOD FOR DETERMINING THE DYNAMIC BIOMECHANICAL CHARACTERISTICS OF A MUSCULOSKELETAL STRUCTURE AND FOR TREATMENT OF MUSCULOSKELETAL DISORDERS

[75] Inventors: Tony S. Keller, Burlington; James B. Lehneman, Winooski, both of Vt.; Arlan W. Fuhr, Phoenix, Ariz.

[73] Assignee: Activator Methods, Inc., Phoenix, Ariz.

[21] Appl. No.: 08/790,003

[22] Filed: Jan. 28, 1997

Related U.S. Application Data

[62] Division of application No. 08/489,102, Jun. 9, 1995, Pat. No. 5,656,017.

[51] Int. Cl.⁶ .................................................. A61B 5/00
[52] U.S. Cl. .................... 600/594; 600/552; 600/595; 601/108; 606/237
[58] Field of Search .................. 600/594, 595, 600/552, 553, 587; 601/107, 108; 606/237, 239

[56] References Cited

U.S. PATENT DOCUMENTS

| | | | |
|---|---|---|---|
| 2,421,354 | 5/1947 | Reiter . | |
| 4,116,235 | 9/1978 | Fuhr et al. | 128/69 |
| 4,498,464 | 2/1985 | Morgan . | |
| 4,682,490 | 7/1987 | Adelman et al. | 73/12 |
| 4,841,955 | 6/1989 | Evans et al. | 128/52 |
| 4,984,127 | 1/1991 | Evans et al. | 361/179 |
| 5,103,806 | 4/1992 | McLeod et al. . | |
| 5,224,469 | 7/1993 | Mocny | 128/55 |
| 5,582,186 | 12/1996 | Wiegand | 128/782 |
| 5,662,122 | 9/1997 | Evans | 128/781 |

*Primary Examiner*—Max Hindenburg
*Attorney, Agent, or Firm*—Leydig, Voit & Mayer, Ltd

[57] ABSTRACT

A non-invasive method for determining the dynamic biomechanical characteristics (frequency response functions and natural frequency) of a musculoskeletal structure is provided. The method generally comprises exciting the musculoskeletal structure over a broad range of frequencies with a low amplitude, high velocity impulsive input force, measuring the input force with a force transducer, detecting the output motion response with an output transducer, processing input force and output response data into time-signal histories with a data acquisition and analysis means or digital computer, transforming the time-signal histories from the time domain to the frequency domain by applying Fourier analysis; and calculating a frequency response function and the natural frequency from the input force and dynamic output response time-signal histories. Having identified the natural frequency of the musculoskeletal structure, the clinician can then mobilize the structure at that frequency in order to maximize the effectiveness of spinal therapy. A hand-held, manually operated impact device for delivering a near optimal, low amplitude, high velocity, impulsive input force over a broad range of frequencies and characterized by a generally half-sinusoidal waveform is also provided.

17 Claims, 6 Drawing Sheets

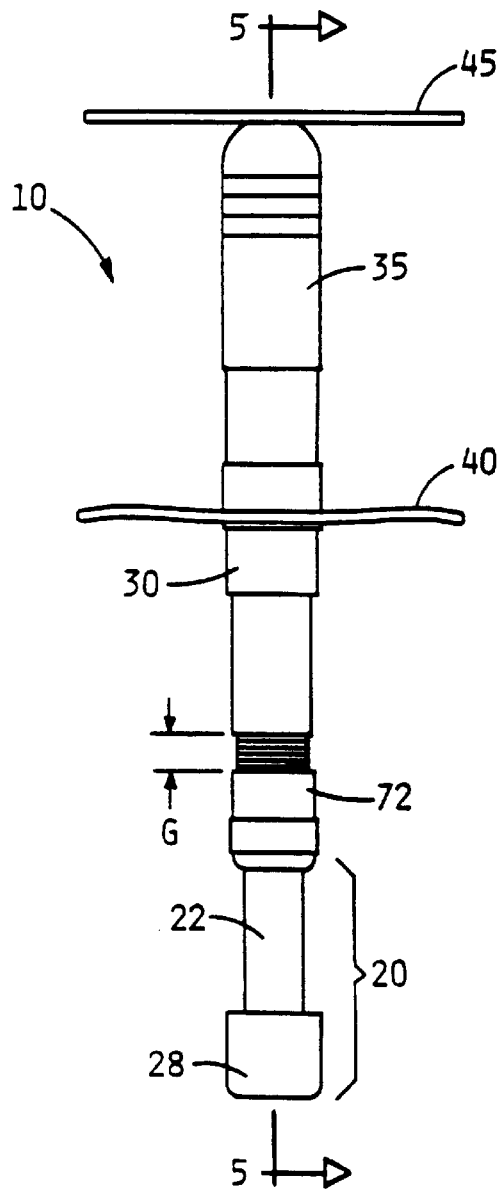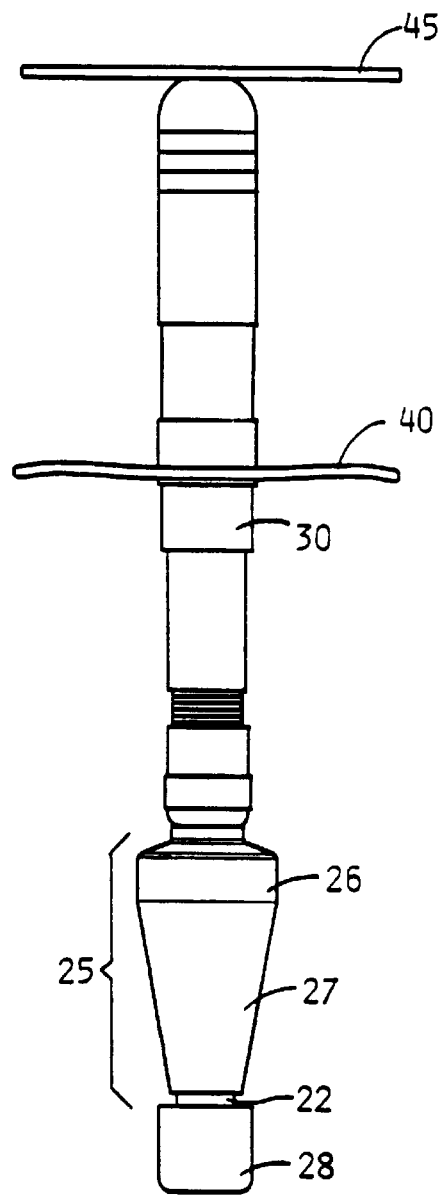
FIG. 4
FIG. 6

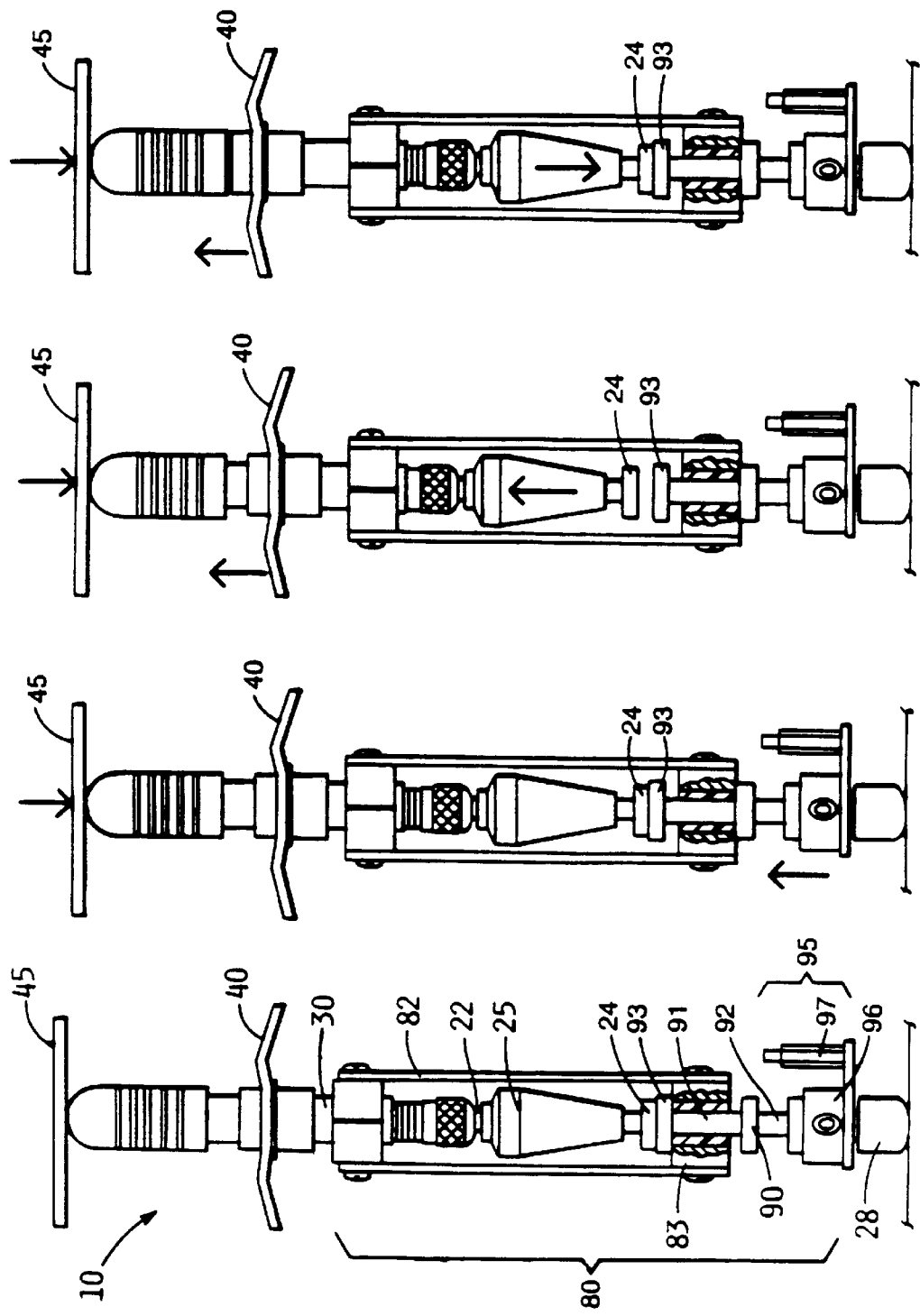

METHOD FOR DETERMINING THE DYNAMIC BIOMECHANICAL CHARACTERISTICS OF A MUSCULOSKELETAL STRUCTURE AND FOR TREATMENT OF MUSCULOSKELETAL DISORDERS

This application is a divisional of U.S. application Ser. No. 08/489,102, filed on Jun. 9, 1995 now U.S. Pat. No. 5,656,017.

BACKGROUND OF THE INVENTION

1. Field of the Invention

The present invention relates generally to chiropractic testing, chiropractic diagnosis, and the treatment of musculoskeletal disorders, and more particularly concerns a non-invasive method for determining the dynamic biomechanical characteristics of a musculoskeletal structure and an apparatus for use in carrying out the same.

2. Description of the Prior Art

The chiropractic art is generally concerned with treating misaligned body structures by manually manipulating the various joints in the human body. Of more specific interest in the art, however, is the spinal column which is comprised of several interconnected bones or vertebrae. Unlike other, less critical body structures, the spinal column must be treated or manipulated with extreme caution because of its link with the central nervous system.

The human spine is susceptible to many different pathologic abnormalities including misalignment, miscellaneous trauma and pain, and degeneration as a result of age or disease. By employing various physical therapy techniques, though, a chiropractor, or one skilled in the chiropractic art, may be able to successfully treat a pathologic spine. Successful treatment will not only relieve any pain or discomfort that the patient might be suffering, but will also improve the overall quality of life of that patient.

One common spinal-adjustment technique involves applying thrusts or forces to the afflicted region of the spine. In particular, this technique involves either "mobilizing" the spine (i.e. passively moving the spine with relatively slow cyclic or oscillatory motion), or "manipulating" the spine (i.e. applying an impulsive thrust or force in a well-defined direction to a specific region of the spine). Depending on professional affiliations, this technique is referred to as chiropractic adjustment, osteopathic manipulation, orthopaedic manual therapy, and/or spinal manipulative therapy.

There are several well known procedures for "manipulating" or administering impulsive thrusts to a spine. One method involves applying one or more rapid thumb thrusts to misaligned or afflicted vertebras. Thumb thrusts, however, tend to be both imprecise in magnitude and location and tiresome to administer. Another technique involves using a manually operated chiropractic adjusting instrument. For instance, U.S. Pat. No. 4,116,235, issued to Fuhr et al. ("Fuhr"), discloses such an instrument. In particular, Fuhr describes a variable, spring-loaded apparatus for delivering a controlled and predetermined impact force or thrust. Heretofore, however, the Fuhr device has been used solely as a therapeutic device for adjusting misaligned vertebrae and has not yet been used as a diagnostic instrument for determining the dynamic biomechanical characteristics of a musculoskeletal structure (or spine).

The ability to Quantify the dynamic biomechanical characteristics of the spinal column of a particular patient provides a chiropractic practitioner or spinal surgeon with several advantages over the current state of the art. Some of these advantages include, but are not limited to: providing a means for obtaining a detailed description of the mechanical status (or health) of the spinal column; providing a method for diagnosing any abnormalities in the spine; providing a way to access the effectiveness of continuing spinal manipulative therapy; and providing a means for appraising the successfulness of spinal fusion surgery. Moreover, by identifying the natural frequency of a spine and by "tuning" impulsive thrusts to that frequency, a chiropractic practitioner can maximize the motion response of the spine while minimizing the magnitude of the thrust. Such a procedure would not only enhance the effectiveness of spinal manipulative therapy, but would also decreases the possibility of damage to the spine during treatment. Furthermore, although the determination of the dynamic mechanical characteristics of a spinal column is an especially important diagnostic tool in the chiropractic art, the various procedures and devices discussed herein have equal applicability to all musculoskeletal structures, and, thus, should not be construed as strictly limited to the chiropractic art.

A chiropractic practitioner can also use mechanical stimuli and natural frequency information to prevent musculoskeletal atrophy and to even stimulate bone formation. There several patents and publications that disclose various methods for maintaining or promoting bone tissue growth, but none of these references disclose a method for preventing musculoskeletal atrophy and stimulating bone formation by subjecting the musculoskeletal structure to thrusts delivered at the natural frequency of the structure. For instance U.S. Pat. No. 5,103,806, issued to McLeod et al. ("McLeod"), discloses a method for promoting bone tissue growth by subjecting a bone to a mechanical load having a low amplitude and a relatively high, but non-specific, frequency (i.e. a frequency range of between about 10 and about 100 hertz). The natural frequency of most musculoskeletal structures, however, is below or at the lower and of this range. More significantly, though, the McLeod patent merely designates a preferred frequency range for treating all bone tissue and does not contemplate or suggest first determining the natural frequency of the particular bone tissue under consideration and then stimulating that bone tissue at its natural frequency.

OBJECTS AND SUMMARY OF THE INVENTION

The primary object of the present invention is to provide a non-invasive method for determining the dynamic biomechanical characteristics of a musculoskeletal structure.

A more specific object of the present invention is to provide a non-invasive method for determining the dynamic biomechanical characteristics of a human spine.

A further object of the present invention is to provide a time and computationally efficient method for determining the dynamic biomechanical characteristics of a musculoskeletal structure. This is achieved by using an apparatus to excite the musculoskeletal structure with a single impulsive input force comprising a broad range of frequencies.

Another object of the present invention is to provide a method of "tuning" the input force to the natural frequency of the musculoskeletal structure of interest.

Still another object of the present invention is to provide a method for obtaining a detailed description of the mechanical status or health of a musculoskeletal structure.

A further object of the present invention is to provide a method for maximizing the effectiveness of spinal manipulative therapy.

Another object of the present invention is to provide a method for accessing the effectiveness of spinal manipulative therapy.

Still another object of the present invention is to provide a method for appraising the successfulness of spinal fusion surgery.

An additional object of the present invention is to provide a method for comparing the dynamic biomechanical characteristics of a given patient with a database of representative dynamic biomechanical characteristics (of both healthy and unhealthy musculoskeletal structures) for use in diagnosing abnormalities in the musculoskeletal structure of that patient.

A further object of the present invention is to provide a method for comparing the dynamic biomechanical characteristics of a given patient with previously derived dynamic biomechanical characteristics of the same patient for use in accessing the effectiveness of continuing chiropractic therapy.

Yet another object of the present invention is to provide a method for stimulating bone formation in a musculoskeletal structure by subjecting the musculoskeletal structure to one or more low amplitude, high velocity impulsive input forces delivered at the natural frequency of the musculoskeletal structure.

A related object of the present invention is to provide an apparatus for use in determining the dynamic biomechanical characteristics of a musculoskeletal structure.

A more specific related object of the present invention is to provide an apparatus for use in determining the dynamic biomechanical characteristics of a human spine.

A further related object of the present invention is to provide an apparatus for delivering a controlled, variable, and consistently repeatable low amplitude, high velocity impulsive force to a musculoskeletal structure.

Another related object of the present invention is to provide an apparatus for use in exciting a musculoskeletal structure over a broad range of frequencies with a single impulsive input force in order to readily determine the vibratory response of the musculoskeletal structure.

An additional related object of the present invention is to provide an apparatus which is "tunable" to the natural frequency of the musculoskeletal structure.

A further related object of the present invention is to provide an apparatus which is capable of delivering an input force having a waveform which is close to half-sinusoidal.

Still another related object of the present invention is to provide an apparatus equipped with an input transducer for measuring the input force delivered to and the musculoskeletal structure and an output transducer for detecting the dynamic output (or motion) response of the musculoskeletal structure.

A further related object of the present invention is to provide an apparatus with a data acquisition and analysis means for collecting and storing input force and dynamic output response data at predetermined time intervals, for generating time-signal histories of the input force and the dynamic output response over a predetermined time duration, and for calculating a frequency response function of the musculoskeletal structure at predetermined frequencies.

Yet another related object of the present invention is to provide an apparatus of the foregoing type which is reliable, precise, and convenient to use.

These and other features and advantages of the invention will become apparent upon reading the following description of a preferred exemplified embodiment of the invention, and upon reference to the accompanying drawings wherein:

BRIEF DESCRIPTION OF THE DRAWINGS

FIG. 4 is a side view of a chiropractic adjusting instrument;

FIG. 6 is a side view of a chiropractic adjusting instrument having a thrust element which is shaped to produce a mechanically tuned frequency; and FIGS. 7A is a side view of a chiropractic adjusting instrument (equipped with a preload frame and a shaped thrust element) before any preload force is applied;

FIGS. 7B is a side view of the chiropractic adjusting instrument after a preload force has been applied;

FIGS. 7C is a side view of the chiropractic adjusting instrument as the handle members are squeezed together and the thrust element retracts within the main body of the instrument; and FIGS. 7D is a side view of the chiropractic adjusting instrument after the handle members have been squeezed together a predetermined distance and the thrust element has been propelled outwardly.

Figure 1A:
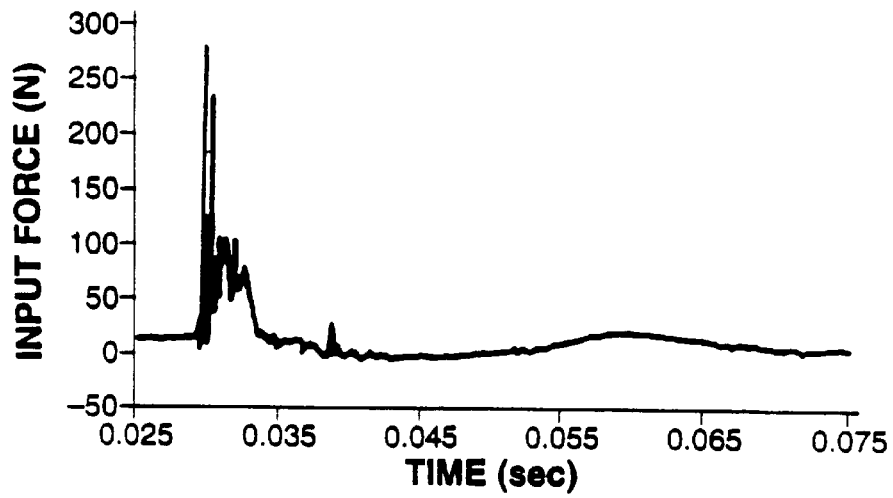
FIGS. 1A–1C are time domain plots of input force, output acceleration, and output velocity, respectively, for a representative impulsive input force.

While the invention will be described and disclosed in connection with certain preferred embodiments and procedures, it is not intended to limit the invention to those specific embodiments. Rather it is intended to cover all such alternative embodiments and modifications as fall within the spirit and scope of the appended claims.

DETAILED DESCRIPTION OF THE PREFERRED EMBODIMENT

In accordance with the present invention, the dynamic biomechanical characteristics of a musculoskeletal structure are obtainable by exciting the musculoskeletal structure over a broad range of frequencies with a single low amplitude, high velocity impulsive input force and by detecting the resulting dynamic output response (or motion response) in the musculoskeletal structure. In particular, the present invention broadly comprises: exciting a musculoskeletal structure (or, more particularly, a spine) with an input force; measuring the input force and detecting the dynamic output response during excitation (where the dynamic output response is either acceleration, velocity, or displacement); collecting and storing dynamic output response data at predetermined time intervals; processing this data into an array to produce time-signal histories of the input force and the dynamic output response; transforming these time-signal histories from the time domain to the frequency domain by applying Fourier analysis; and calculating a frequency response function by taking the ratio of either: (1) the Fourier transform of the time-signal history of the input force over the Fourier transform of the time-signal history of the dynamic output response; or, alternatively (2) the Fourier transform of the dynamic output response over the Fourier transform of the time-signal history of the input force. A complete inventory of frequency response functions are listed in TABLE 1 below.

TABLE 1

FREQUENCY RESPONSE FUNCTIONS

| | |
|---|---|
| Accelerance | Output Acceleration/Input Force |
| Effective Mass | Input Force/Output Acceleration |
| Mobility | Output Velocity/Input Force |
| Impedance | Input Force/Output Velocity |
| Dynamic Compliance | Output Displacement/Input Force |
| Dynamic Stiffness | Input Force/Output Displacement |

It should be noted that, in the context of the present invention, the dynamic biomechanical characteristics of a musculoskeletal structure include not only the frequency response functions listed above in TABLE 1, but also natural frequency. It should be further noted that there are two principle techniques for measuring the frequency response function of a structure. A "driving point" frequency response function is obtained when the input and response measurements are taken at the same point and in the same direction. In contrast, a "transfer" frequency response function is obtained when input measurements are taken at one point (typically at the input device) and response measurements are taken at a different point (typically at the structure being analyzed). On the whole, "transfer" technique measurements should be regarded as the preferable way to measure the response of any system since they are inherently more reliable than "driving point" technique measurements. In analyzing musculoskeletal structures, however, it is usually necessary to use "driving point " technique measurements since it is generally impossible or exceedingly impractical to rigidly attach an output transducer to a musculoskeletal structure. Thus, for the purpose of describing the preferred embodiment of the present invention, all frequency response functions discussed herein are of the "driving point" type, unless otherwise indicated.

Figure 1B:
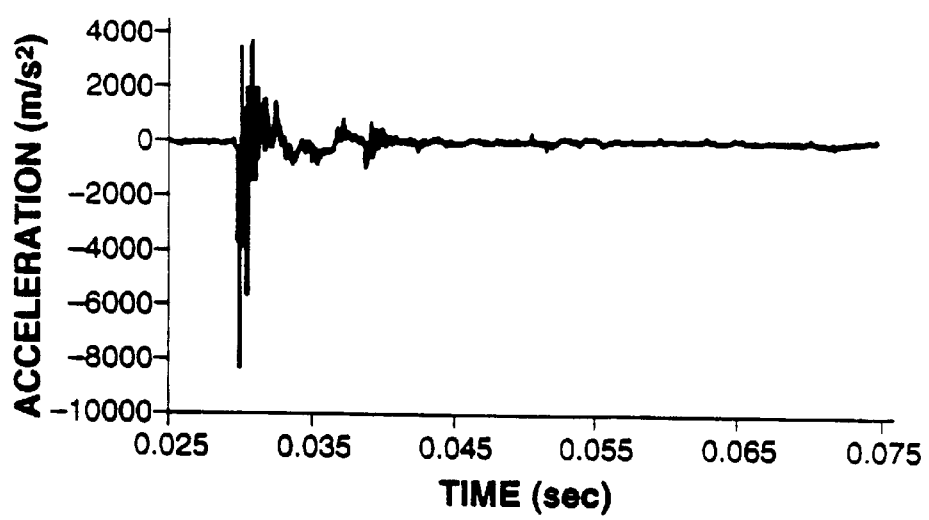
Figure 1C:
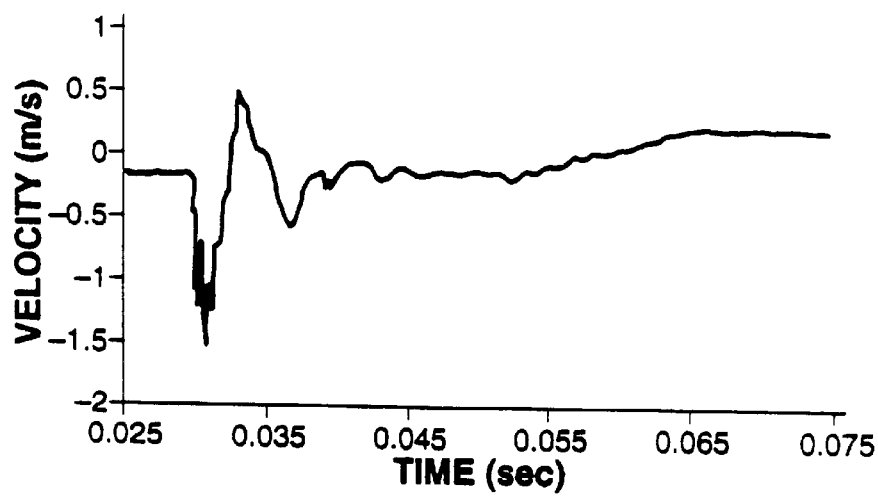

Turning now to the drawings, FIGS. 1A–1C show representative time domain plots of input force versus time, output acceleration versus time, and output velocity versus time, as generated using the method of the present invention. In particular, the second lumbar vertebras of a thirty-nine year old healthy male patient was excited in the posterior-anterior direction with a single low amplitude, high velocity impulsive input force comprising a broad range of frequencies. During this period of excitation, the input force was continuously detected using a force transducer and the output acceleration was continuously detected using an accelerometer. As clearly shown in FIGS. 1A and 1B, the input force and the output acceleration vary substantially with time. For this reason, input force and output acceleration data was collected and stored at very short, predetermined time intervals (i.e. on the order of 0.000020 seconds). By loading this data into an array, time-signal histories of the input force and output acceleration were created. For the purposes of describing the present invention, the term "time-signal history" simply refers to a sequential collection of data at each predetermined time interval over the entire excitation period. The time-signal histories of the input force and the output acceleration are shown in FIGS. 1A and 1B, respectively.

The time-signal history of the output velocity, depicted in FIGS 1C, was not directly measured. Instead, it was indirectly derived by integrating the time-signal history of the output acceleration. Here, Simpson's rule was used as the specific integration method, but other integration methods, including the Triangle rule, are also permissible. It will be appreciated by those skilled in the art, however, that the time-signal history of the output velocity is also directly derivable by using an integrator amplifier. In addition, a time-signal history of the output displacement, if desired, is derivable either directly (i.e. by using a displacement transducer) or indirectly (i.e. by integrating the time-signal history of the output velocity).

Figure 2A:
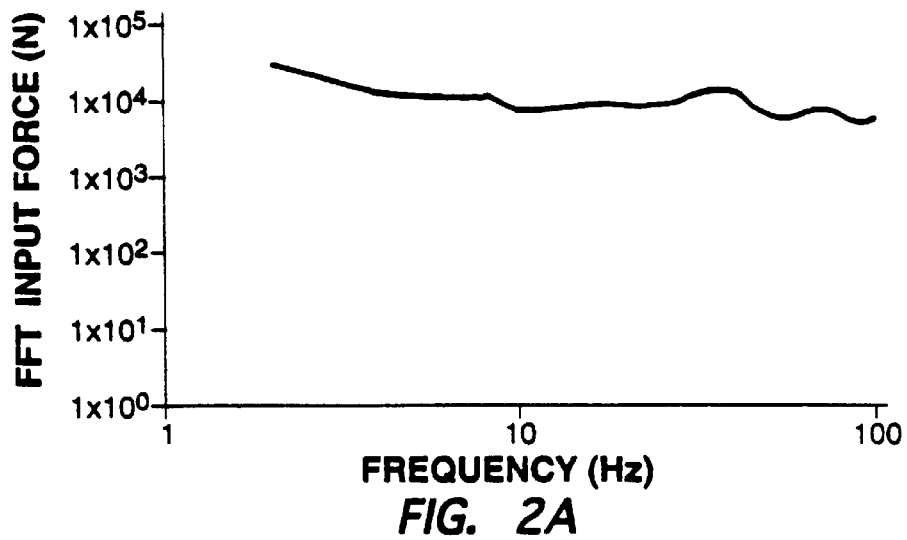
FIGS. 2A–2C are the corresponding frequency domain plots of input force, output acceleration, and output velocity, respectively, derived from the time domain plots in FIGS. 1A–1C.
Figure 2B:
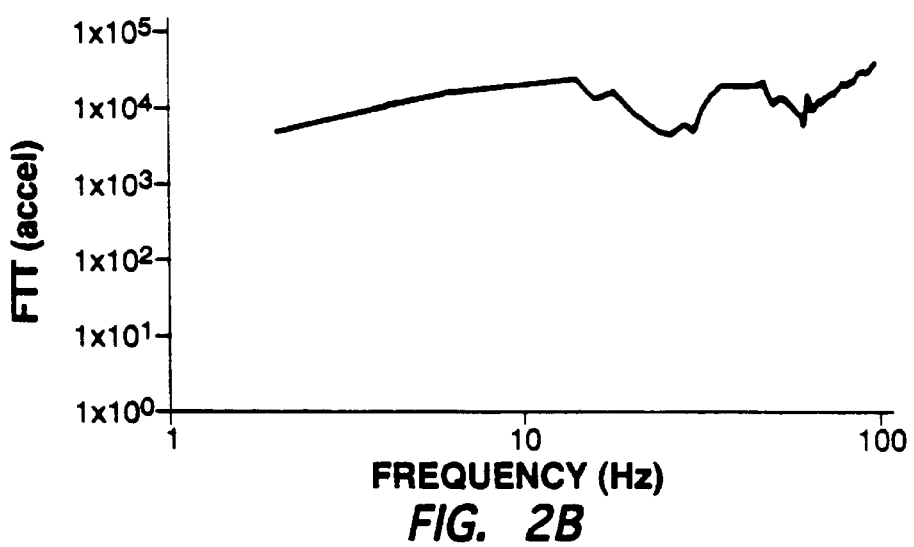
Figure 2C:
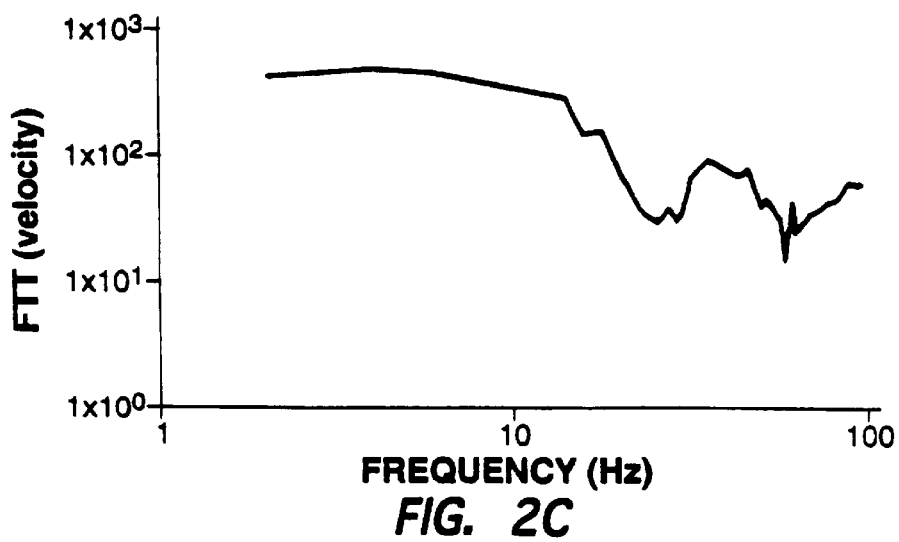

The time-signal histories of input force, output acceleration, and output velocity were transformed from the time domain to the frequency domain by applying a Fourier transform to each time-signal history. Frequency domain plots of input force, output acceleration, and output velocity are shown in FIGS. 2A, 2B, and 2C. respectively. The use of a fast Fourier transform ("FFT"), and not a regular Fourier transform, was used since the data was in digital, and not analog, format.

Figure 3:
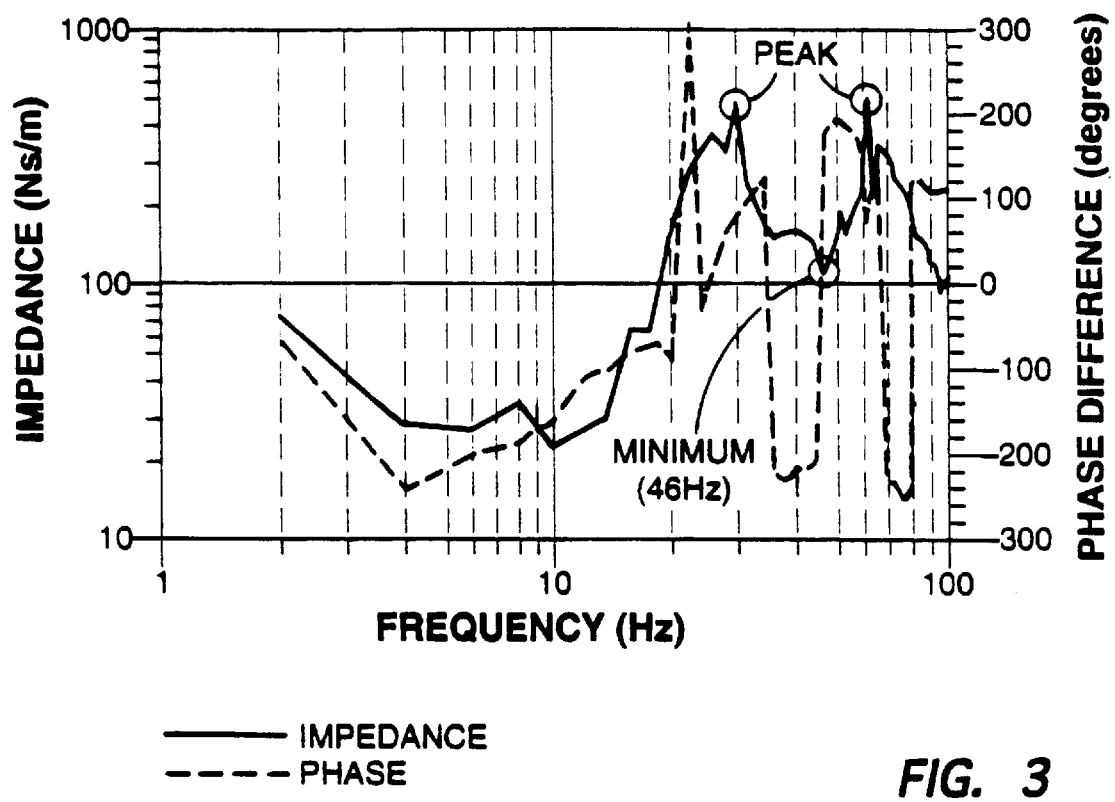
FIG. 3 is a plot of impedance as a function of frequency as generated from the input force and output acceleration plots in FIGS. 2A and 2C, respectively.

As listed in TABLE 1, impedance is simply the ratio of input force over output velocity. As such, a frequency domain plot of "driving point" impedance was created by taking the ratio of the FFT array of the time-signal history of the input force over the FFT array of the time-signal history of the output velocity. Further, a phase difference plot was also generated, where phase difference is simply the phase of the input force minus the phase of the output velocity. Plots of both impedance and phase difference versus frequency are shown in FIG. 3. Although the calculation of impedance is specifically described herein, it will be readily understood by those skilled in the art that any (and all) of the frequency response functions listed in TABLE 1 are obtainable simply by taking the appropriate ratio.

Like all mechanical systems, musculoskeletal structures exhibit increased motion at some frequencies and decreased motion at other frequencies. In particular, the frequency associated with maximum motion is referred to as the "natural frequency" and the response of a mechanical system excited at its natural frequency is noticeably magnified. For instance, the dynamic output response of a normal spine is typically amplified by a factor of two to three when the input force is delivered at the natural frequency. However, since each person is unique in terms of dynamic biomechanical characteristics—including unique in terms of natural frequency—the ability to "tune" the input force to the natural frequency of the musculoskeletal structure of the person being treated is especially important. For instance, by "tuning" the input force to the natural frequency of a particular spine, the dynamic output response of that spine can be maximized while, at the same time, the input force necessary to fully excite that spine can be minimized. This not only significantly enhances the effectiveness of spinal manipulative therapy, but also decreases the possibility of spinal damage during such treatment. Accordingly, the ability to ascertain the natural frequency of a musculoskeletal structure is an important aspect of the present invention. Further, the ability to "tune" the input force to the natural frequency of the musculoskeletal structure in question is also an important aspect of the present invention.

Musculoskeletal structures, as heavily damped structures, are characterized by distinctive descriptive frequency response functions. For instance, as illustrated in FIG. 3, the "driving point" impedance of the second lumbar vertebras of the thirty-nine year old healthy male patient is characterized by a relatively flat and muted impedance at low frequency values and a "peak-minimum-peak" waveform sequence at higher frequency values. Like all heavily damped structures, the minimum impedance value in the "peak-minimum-peak" waveform sequence is usually the natural frequency of this particular vertebrae. Here, the natural frequency is clearly 46 hertz. Furthermore, this natural frequency determination is verifiable by examining the accompanying phase difference plot. In particular, the natural frequency of a heavily damped structure, such as a musculoskeletal structure, is characterized by: (1) a phase difference that rapidly transitions from an extreme negative (or positive) phase difference to an extreme positive (or negative) phase difference, or visa versa; and (2) a phase difference that is zero or close to zero. Since both of these characteristics also occur at 46 hertz, the natural frequency of this particular vertebras is thus confirmed.

It should be appreciated by those skilled in the art that the natural frequency of a musculoskeletal structure can alternatively be found by using the other frequency response functions listed in TABLE 1, namely accelerance, effective mass, mobility, dynamic compliance, and dynamic stiffness. However, because these terms are all ratios involving input force and dynamic output response, the natural frequency is determined by finding the frequency associated with either the minimum or maximum frequency response function value and then confirming this determination by examining the phase difference graph. In particular, for effective mass, impedance, and dynamic stiffness (i.e. where input force is the numerator of the frequency response function ratio), the natural frequency of a musculoskeletal structure is first determined by finding frequency associated with the minimum value in the "peak-minimum-peak" waveform sequence. On the other hand, for accelerance, mobility, and dynamic compliance (i.e. where input force is the denominator of the frequency response function ratio), the natural frequency of a musculoskeletal structure is first determined by finding frequency associated with the maximum value in a "minimum-peak-minimum" waveform sequence.

Accordingly, by applying the methodology of the present invention, the dynamic biomechanical characteristics of a given musculoskeletal structure, including natural frequency, can be ascertained. Further, once the dynamic biomechanical characteristics of a given musculoskeletal structure are known, this information can be utilized not only as a diagnostic tool, but also as a means for individually tailoring chiropractic and rehabilitative therapy.

For instance, a detailed description of the mechanical status (or health) of the musculoskeletal structure of a given patient is provided by quantifying the dynamic biomechanical characteristics of that patient. More specifically, though, any abnormalities in the musculoskeletal structure of that patient can be diagnosed by comparing the dynamic biomechanical characteristics of that patient with a "normal database". Preferably, such a database would include standardized dynamic biomechanical characteristic data based on various factors such as age, size, and sex. A direct comparison would permit a practitioner to readily ascertain whether the patient is within "normal limits". Likewise, the effectiveness of ongoing chiropractic therapy could be assessed simply by comparing a current listing of the dynamic biomechanical characteristics of the patient with a previously derived listing of the dynamic biomechanical characteristics of the same patient.

While information regarding the frequency response function of a particular musculoskeletal structure is useful as a diagnostic tool, information regarding the natural frequency is especially useful in crafting future treatment sessions. In particular, the inventors have discovered that subjecting a musculoskeletal structure to low amplitude, high velocity impulsive input forces delivered at the natural frequency of the musculoskeletal structure can not only prevent musculoskeletal atrophy but stimulate bone formation. The natural frequency of musculoskeletal structures, however, tends to be very low. For instance, the natural frequency of a healthy human spine subjected to a posterior-anterior mechanical stimulus, such as that routinely delivered by a chiropractic practitioner, is normally between about 30 and 50 hertz. As such, a chiropractic practitioner or physician may attempt to promote bone growth by arbitrarily subjecting the bone to stimuli in this range. However, the most effective treatment would be to first identify the natural frequency of the particular musculoskeletal structure being treated and then subject the musculoskeletal structure to one or more low amplitude, high velocity impulsive force delivered at the natural frequency.

In addition to the methods discussed herein, the present invention is also directed at an apparatus for use in determining the dynamic biomechanical characteristics of a musculoskeletal structure. In particular, the apparatus of the present invention broadly comprises: an impact device for delivering a low amplitude, high velocity impulsive input force over a broad range of frequencies to a musculoskeletal structure; an input transducer for measuring the input force delivered to the musculoskeletal structure; a response transducer for detecting the dynamic output response of the musculoskeletal structure; and a data acquisition and analysis means: (1) for collecting and storing input force and dynamic output response data at predetermined time intervals; (2) for generating time-signal histories of the input force and the dynamic output response over a predetermined time duration; and (3) for calculating a frequency response function of the musculoskeletal structure at predetermined frequencies. As described above, the frequency response function can be any of the ratios identified in TABLE 1, provided that the numerator and the denominator of the ratio are either the Fourier transform of the time-signal history of the input force or the Fourier transform of the time-signal history of the dynamic output response.

The impact device is specifically provided for delivering a low amplitude, high velocity impulsive input force comprising a broad range of frequencies. A first embodiment of the impact device is disclosed in the aforementioned Fuhr patent. In particular, the Fuhr device, as shown in FIG. 4, is a manually operated chiropractic posterior-anterior adjusting instrument 10 which generally comprises: a thrust element 20; a main body 30; an and cap 35; a first handle member 40; a second handle member 45; a spring means 60 for propelling the thrust element 20 outwardly; and a trigger means for actuating the spring means 60.

Figure 5:
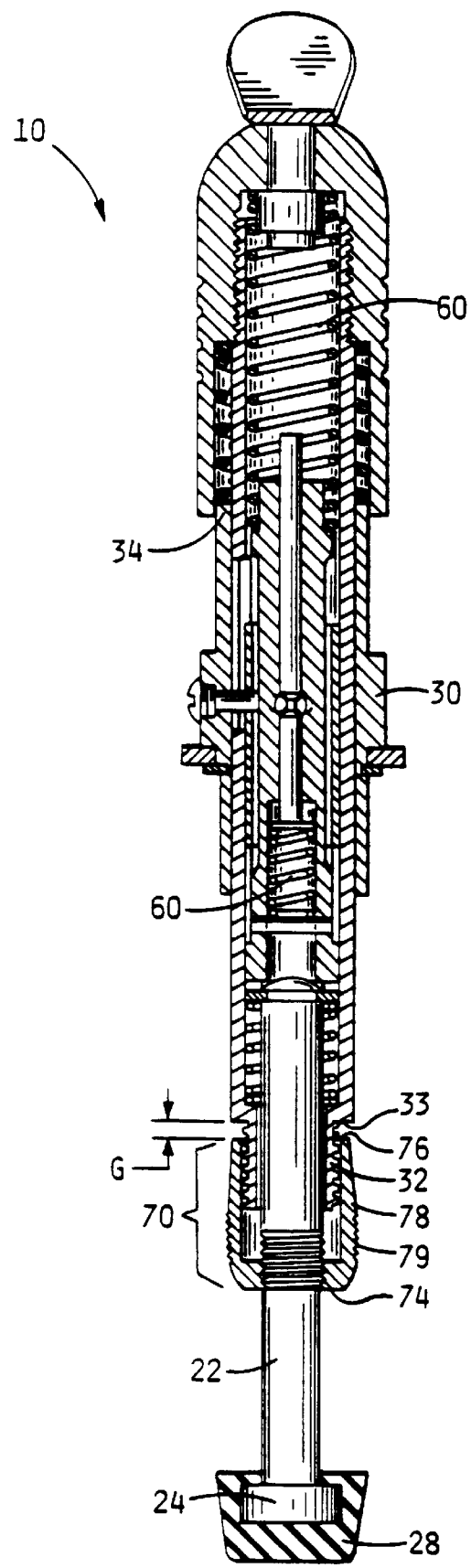
FIG. 5 is a cross-sectional view of the chiropractic adjusting instrument taken along line 5—5 in FIG. 4.

As best shown in FIG. 5, the thrust element 20 of the chiropractic adjusting instrument 10 comprises a shank portion 22 and an end portion 24. Preferably, the thrust element 20 also comprises a removable body contact member 28, disposed on the end portion 24, which is made of a resilient material such as rubber, soft plastic, or the like. The main body 30 has a first end 32, which longitudinally slidably receives the shank portion 22 of the thrust element 20, and a second end 34. The end cap 35 is both swivelly and longitudinally slidably mounted on the second end 34 of the main body 30. As shown in FIG. 4, the first and second handle members 40, 45 are arranged in spaced relation to one another. More specifically, the first handle member 40 is rotatably disposed on the main body 30, the second handle member 45 is fixedly disposed on the end cap 35, and the first and second handle members 40, 45 are squeezably disposed relative to one another. In operation, as the first and second handle members 40, 45 are squeezed together, the shank portion 22 of the thrust element 20 retracts inwardly within the main body 30 which compresses the spring means 60. Ultimately, when the first and second handle members 40, 45 have been squeezed together a predetermined distance, the trigger means releases or actuates the spring means 60 and the thrust element 20 is propelled rapidly outwardly. For a complete disclosure of the structure and operation of the trigger means, see column 3, line 51 through column 4, line 62 of the Fuhr patent.

Preferably, the chiropractic adjusting instrument 10 further comprises a calibration means 70 for controlling the amount that the shank portion 22 of the thrust element 20 retracts within the main body 30 when the first and second handle portions 40, 45 are squeezed together, for controlling the amount of potential energy imposed on the spring means 60, and, more particularly, for adjusting the amplitude of the input force delivered to the musculoskeletal structure. In the illustrated embodiment, the calibration means 70 comprises an adjustment knob 72 having an internally threaded end 74, a non-threaded end 76, and a sleeve portion disposed therebetween 78. As shown in FIG. 5, the internally threaded end 74 is screwably disposed on the shank portion 22 of the thrust element 20 such that a gap G, or initial spacing, exists between the non-threaded end 76 of the adjustment knob 72 and the flange 33 of the main body 30. In use, when the first and second handle members 40, 45 are squeezed together, the non-threaded end 76 engages the flange 33. As such, the gap G not only predefines the amount that the shank portion 22 of the thrust element 20 can retract within the main body 30, but also controls the amount of potential energy imposed on the spring means 60 as well as the magnitude of the input force that is delivered by the adjusting instrument 10 (i.e. a larger gap G denotes a higher amplitude input force). Calibration of the chiropractic adjustment instrument 10 is thus accomplished simply by turning or screwing the adjustment knob 72 to the desired position. In the preferred embodiment, the sleeve portion 78 of the adjustment knob 72 is also provided with a knurled portion 79 which facilitates the turning and positioning of the adjustment knob 72.

In accordance with certain objects of the present invention, the input force delivered by the impact device is also adjustable or "tunable" to the natural frequency of the musculoskeletal structure being examined. In particular, the input force provided by the chiropractic adjusting instrument 10 is "tuneable" by varying the mass of the thrust element 20, by varying the stiffness of the removable contact member 28, or, alternatively, by varying the stiffness (or spring constant) of the spring means 60. Further, although the input force is "tunable" the input force of the chiropractic adjusting instrument 10 depicted in FIGS. 4 and 5 is characterized by a damped-sinusoidal waveform which is generally not the best signal for use in determining the dynamic biomechanical characteristics of a musculoskeletal structure.

One embodiment of a "mechanically tuned" chiropractic adjusting instrument is illustrated in FIG. 6. In this embodiment, a shaped mass 25, comprising a generally cylindrical portion 26 and a generally conical portion 27 is arranged on the shank portion 22 of the thrust element 20. In particular, the generally conical portion 27 tapers inwardly from the generally cylindrical portion 26. Moreover, the shaped mass 25 is arranged on the thrust element 20 such that the generally cylindrical portion 26 faces the first handle member 40 while the generally conical portion 27 faces the removable body contact member 28. This particular embodiment is mechanically tuned to a particular frequency. More importantly, though, the frequency at which the chiropractic adjustment instrument 10 is mechanically tuned to can be varied—between a range of about 1 hertz to about 60 hertz—simply by changing the mass, shape, and/or arrangement of the shaped mass 25.

The chiropractic adjusting instrument 10 can alternatively be "tuned" by changing the stiffness of the removable body contact member 28 or the stiffness of the spring means 60. For instance, by varying the stiffness of the body contact member 28 between the range of about 30 durometer to about 80 durometer, the mechanical tuning of the chiropractic adjusting instrument 10 can be appreciably modified.

An alternative embodiment of the impact device comprises either an electro-mechanical or a pneumatic impulsive delivery system (not shown) which, unlike the manual chiropractic adjusting instrument 10, delivers an input force characterized by a generally half-sinusoidal waveform. As a general rule, a half-sinusoidal waveform is the optimal signal for use in determining the dynamic biomechanical characteristics of a musculoskeletal structure because such a signal generates a lot or energy over a broad range of frequencies. Electro-mechanical and pneumatic impulsive delivery systems are also commonly used with the "transfer" technique discussed above (i.e. input is measured at one point, typically at the impact device itself, and output is measured at another point, typically at the structure being analyzed), and are thus generally ill-suited for human testing. However, should the "driving point" technique be used (i.e. both input and output are measured at the impact device), either one of these systems may alternatively be used in human musculoskeletal testing.

It was discovered by the inventors that the use of a preload frame 80 attached to the chiropractic adjusting instrument 10 not only reduces human error and increases repeatability, but also delivers impacts similar to those of an electro-mechanical or pneumatic impulsive delivery system (i.e. the waveform of the impacts are closer to half-sinusoidal than damped-sinusoidal). For instance, a chiropractic adjusting instrument 10 equipped with a preload frame 80 was used to impart the input force depicted in FIG. 1A which is characterized by a roughly half-sinusoidal waveform. As further shown in FIG. 2A this signal generates a lot or energy over a broad range of frequencies (i.e. the FFT input force versus frequency plot is relatively flat). For these reasons, a chiropractic adjusting instrument 10 equipped with a preload frame 80, as shown in FIG. 7A, exemplifies the preferred embodiment of a manually operated impact device.

As shown in FIGS. 7A, the preload frame 80 is readily attachable to the chiropractic adjusting instrument 10 and generally comprises a truss portion 82, a bearing portion 83, an impact stylus 90, and a body contact member 28. In particular, the truss portion 82 is fixedly attached to the main body 30 of the chiropractic adjusting instrument 10 and the bearing portion 83 fixedly attached to the truss portion 82. The impact stylus 90 has a first portion 91 which is slidably disposed within the bearing portion 83 and a second portion 92 projects outwardly from the bearing portion 83. The first portion 91 of the impact stylus 90 also has an anvil surface portion 93 which normally abuts the end portion 24 of the thrust element 20. The removable body contact member 28 is attached to the second portion 92 of the impact stylus 90.

Ideally, the chiropractic adjusting instrument 10 not only comprises a preload frame 80, but is also equipped with a shaped mass 25 which is mechanically tuned to the natural frequency of the musculoskeletal structure under examination. As discussed above, the shaped mass 25 is arranged on the shank portion 22 of the thrust element 20. In the illustrated embodiment, the chiropractic adjusting instrument also comprises a transducer head 95, disposed between the body contact member 28 and the second portion 92 of the impact stylus 90. More specifically, the transducer head 95 comprises an "impedance head", as shown in FIG. 7A, for ascertaining "driving point" impedance. In particular, the impedance head is equipped with a load cell 96 for measuring input force and an accelerometer 97 for detecting dynamic output acceleration. Although the illustrated embodiment specifically discusses an impedance head 95 equipped with an accelerometer, it will be understood by those skilled in the art that the transducer head 95 may alternatively comprise an velocity transducer or a displacement transducer in lieu of the accelerometer 97.

The step-by-step operation of a preload frame 80 equipped chiropractic adjusting instrument 10 is illustrated in FIGS. 7A through 7D. Specifically, FIG. 7A depicts the assembly as it exists before any preload is applied (i.e. before the assembly is pressed against a musculoskeletal structure). Once a preload force is applied to the assembly, though, the first portion 91 of the impact stylus 90 is urged upwardly within the bearing portion 83 which, in turn, urges the thrust element 20 to retract within the main body 30, as shown in FIG. 7B. When the first handle and second handle members 40, 45 are then squeezed together, as shown in FIG. 7C, the shank portion 22 of the thrust element 20 further retracts within the main body 30 while the end portion 24 of the thrust element 20 moves away from the anvil surface portion 93 of the first portion 91 of the impact stylus 90. Once the first and second handle members 40, 45 have been squeezed together a predetermined distance, though, the thrust element 20 is propelled outwardly by the spring means and the end portion 24 of the thrust element strikes the anvil surface portion 93 of the first portion 91 of the impact stylus 90, as illustrated in FIG. 7D. This particular apparatus delivers an input force to the musculoskeletal structure which, like the electro-mechanical or pneumatic impulsive deliver systems, is characterized by a generally half-sinusoidal waveform.

Aside from the impact device, the apparatus of the present invention further comprises an input transducer, an output transducer, and a data acquisition-and analysis means. In particular, the input transducer is provided for detecting the input force delivered to the musculoskeletal structure. In the illustrated embodiment, depicted in FIG. 7A, the input transducer comprises a load cell 96 which is attached to the transducer head 95.

The response transducer, on the other hand, is provided for detecting the dynamic output response of the musculoskeletal structure. Depending on the frequency response function desired, the response transducer can either comprise an acceleration transducer (i.e. an accelerometer 97), a velocity transducer (i.e. an integrator amplifier), or a displacement transducer (i.e. a motion sensor). However, if a displacement transducer is used, only dynamic compliance and dynamic stiffness may be calculated since only these two frequency response functions use output displacement. On the other hand, if an acceleration transducer is used all of the frequency response functions listed in TABLE 1 may be determined since the time-signal history of the output velocity is indirectly derivable by integrating the time-signal history of the output acceleration and since the time-signal history of the output displacement is similarly derivable by integrating the time-signal history of the output velocity. As such, an accelerometer 97 is generally the preferred choice. Further, since it is generally necessary to use "driving point" measurements in analyzing musculoskeletal structures, the output transducer must detect measurements at the same point and in the same direction as the input transducer. Thus, the accelerometer 97, like the load cell 96, is preferably attached to the transducer head 95.

The data acquisition and analysis means (not shown) is provided for collecting and storing input force and dynamic output response data at predetermined time intervals, for generating time-signal histories of the input force and the dynamic output response over a predetermined time duration, and for calculating frequency response functions of the musculoskeletal structure at predetermined frequencies. For this type of testing, it is generally necessary to obtain data at exceedingly short time intervals. As such, it is necessary to use a relatively high sampling frequency (i.e. on the order of 50 kilohertz). Although the time duration is typically very short (i.e. on the order of 0.0160.250 seconds) a vast amount of data must nevertheless be collected and stored. For example, a sampling frequency of 50 kilohertz translates into a data collection rate of every 0.00002 seconds. Further, for a time duration of only 0.160 seconds, 8000 predetermined time intervals—or individual times at which both input force and dynamic output response data must be collected —are required. Moreover, since this data must also be transformed and manipulated, a relatively sophisticated data acquisition and analysis means is required. In the preferred embodiment, the data acquisition and analysis means comprises a digital computer.

In addition, since input force and dynamic output response data must be in digital format in order to be recognized by the computer, an analog-digital converter (not shown) is also required. A 12-bit analog-digital converter is suitable for this purpose. Likewise, since digital computers can only processes data in digital format, a "fast Fourier transform"—as opposed to a "Fourier transform"—must be applied to the time-signal histories.

As an added feature of the present invention, the data acquisition and analysis means should further comprise a display means for generating graphs of input force versus time, dynamic output response versus time, and frequency response function versus frequency.

Thus, the data acquisition and analysis means, or computer, should have the capacity to: (1) derive a time-signal history of the output velocity by integrating the time-signal history of the output acceleration; (2) derive a time-signal history of the output displacement by integrating the time-signal history of the output velocity; (3) perform FFT's of the time-signal histories of the input force, the output acceleration, the output velocity, and the output displacement; and (4) generate graphical representations of the dynamic biomechanical characteristics of the musculoskeletal structure including frequency response functions.

We claim as our invention:

1. A non-invasive method for determining the dynamic biomechanical characteristics of a musculoskeletal structure, the dynamic biomechanical characteristics comprising frequency response functions and natural frequency, the method comprising the steps of:

exciting the musculoskeletal structure over a broad range of frequencies with a low amplitude, high velocity impulsive input force, the input force producing a dynamic output motion response in the musculoskeletal structure;

measuring the input force and detecting the dynamic output motion response during excitation;

collecting and storing input force and dynamic output motion response data at predetermined time intervals;

processing the input force and dynamic output motion response data to produce a time-signal history of the input force and the dynamic output motion response;

transforming the time-signal histories of the input force and the dynamic output motion response from the time domain to the frequency domain by applying a Fourier transform to each time-signal history; and calculating a frequency response function of the musculoskeletal structure at predetermined frequencies.

2. The method as set forth in claim 1 wherein the dynamic output motion response is output acceleration.

3. The method as set forth in claim 1 wherein the dynamic output motion response is output velocity.

4. The method as set forth in claim 1 wherein the dynamic output motion response is output displacement.

5. The method as set forth in claim 1 wherein the frequency response function is the ratio of:

the Fourier transform of the time-signal history of the input force/the Fourier transform of the time-signal history of the dynamic output motion response.

6. The method as set forth in claim 5 wherein the Fourier transform is a fast Fourier transform.

7. The method as set forth in claim 5 further comprising the steps of:

plotting the frequency response function versus frequency;

plotting phase difference versus frequency, wherein phase difference is phase of the input force minus phase of the dynamic output motion response;

ascertaining the natural frequency of the musculoskeletal structure by examining the characteristics of the frequency response function plot; and verifying the natural frequency of the musculoskeletal structure by examining the phase difference plot.

8. The method as set forth in claim 1 wherein the frequency response function is the ratio of:

the Fourier transform of the time-signal history of the dynamic output motion response/the Fourier transform of the time-signal history of the input force.

9. The method as set forth in claim 8 wherein the Fourier transform is a fast Fourier transform.

10. The method as set forth in claim 8 further comprising the steps of:

plotting the frequency response function versus frequency;

plotting phase difference versus frequency, wherein phase difference is phase of the input force minus phase of the dynamic output motion response;

ascertaining the natural frequency of the musculoskeletal structure by examining the characteristics of the frequency response function plot; and verifying the natural frequency of the musculoskeletal structure by examining the phase difference plot.

11. The method as set forth in claim 1 further comprising the step of:

tuning the input force to the natural frequency of the musculoskeletal structure.

12. The method as set forth in claim 11 further comprising the step of:

re-exciting the musculoskeletal structure at the natural frequency.

13. The method as set forth in claim 7 further comprising the step of:

comparing the dynamic biomechanical characteristics of the patient with a database of standardized dynamic biomechanical characteristics for the purpose of diagnosing abnormalities in the musculoskeletal structure of the patient.

14. The method as set forth in claim 7 further comprising the step of:

comparing the dynamic biomachanical characteristics of the patient with previously derived dynamic biomechanical characteristics of the same patient for the purpose of assessing the effectiveness of chiropractic treatment.

15. The method as set forth in claim 10 further comprising the step of:

comparing the dynamic biomechanical characteristics of the patient with a database of standardized dynamic biomechanical characteristics for the purpose of diagnosing abnormalities in the musculoskeletal structure of the patient.

16. The method as set forth in claim 10 further comprising the step of:

comparing the dynamic biomechanical characteristics of the patient with previously derived dynamic biomechanical characteristics of the same patient for the purpose of assessing the effectiveness of chiropractic treatment.

17. The method as set forth in claim 1 wherein the musculoskeletal structure is a spinal column.

* * * * *